(12) United States Patent
Zapata Perez

(10) Patent No.: US 8,303,479 B2
(45) Date of Patent: Nov. 6, 2012

(54) BIOPHYSIOLOGICAL REGULATOR FOR THERAPEUTIC TREATMENTS

(75) Inventor: Carlos Zapata Perez, Madrid (ES)

(73) Assignee: Laboratorios BZ I&D, S.L., Madrid (ES)

( * ) Notice: Subject to any disclaimer, the term of this patent is extended or adjusted under 35 U.S.C. 154(b) by 302 days.

(21) Appl. No.: 12/595,022

(22) PCT Filed: Jan. 16, 2008

(86) PCT No.: PCT/ES2008/000023
§ 371 (c)(1),
(2), (4) Date: Oct. 7, 2009

(87) PCT Pub. No.: WO2009/007472
PCT Pub. Date: Jan. 15, 2009

(65) Prior Publication Data
US 2010/0069703 A1    Mar. 18, 2010

(30) Foreign Application Priority Data
Jul. 9, 2007    (ES) .................................. 200701921

(51) Int. Cl.
*A61N 1/00*    (2006.01)
*A61N 2/00*    (2006.01)
*A61B 17/52*    (2006.01)
(52) U.S. Cl. ............................. 600/13; 600/9
(58) Field of Classification Search ................ 600/13, 600/9
See application file for complete search history.

(56) References Cited

U.S. PATENT DOCUMENTS

| 7,258,659 B2 * | 8/2007 | Anninou et al. ............... 600/13 |
| 2003/0050527 A1 * | 3/2003 | Fox et al. .................... 600/13 |
| 2005/0033380 A1 * | 2/2005 | Tanner et al. .................. 607/45 |
| 2005/0113630 A1 * | 5/2005 | Fox et al. .................... 600/13 |
| 2005/0182287 A1 * | 8/2005 | Becker ......................... 600/13 |
| 2006/0106274 A1 * | 5/2006 | Thomas et al. ................. 600/13 |
| 2008/0263680 A1 * | 10/2008 | Bertin .......................... 726/30 |

FOREIGN PATENT DOCUMENTS
GB     2413284    * 10/2005
WO    WO0215771  * 2/2002

* cited by examiner

*Primary Examiner* — Samuel Gilbert
*Assistant Examiner* — Sunita Reddy
(74) *Attorney, Agent, or Firm* — Collen IP; Donald J. Ranft

(57) ABSTRACT

The invention relates to a biophysiological regulator for therapeutic treatments, including brain stimulation coils (7) which generate current using a microcontroller (11). The invention includes a second microcontroller (16), a liquid crystal display (17), a selector (21) for selecting pre-recorded programs and a connection port (20) for an external device (19) which is provided with a speaker (24) and LEDs that indicate whether or not the battery is charged (18), the regulator is connected (27), an application is underway (26) and the battery is low (25), and an internal program (28) which regulates the frequency and typology of the output wave and the time. The invention also includes a tamper protection system formed by a microcontroller (29) inside a special connector (30) built into the assembly (applicator and cable), in which the internal software of the device reads the serial number located inside the microcontroller of the connector.

2 Claims, 1 Drawing Sheet

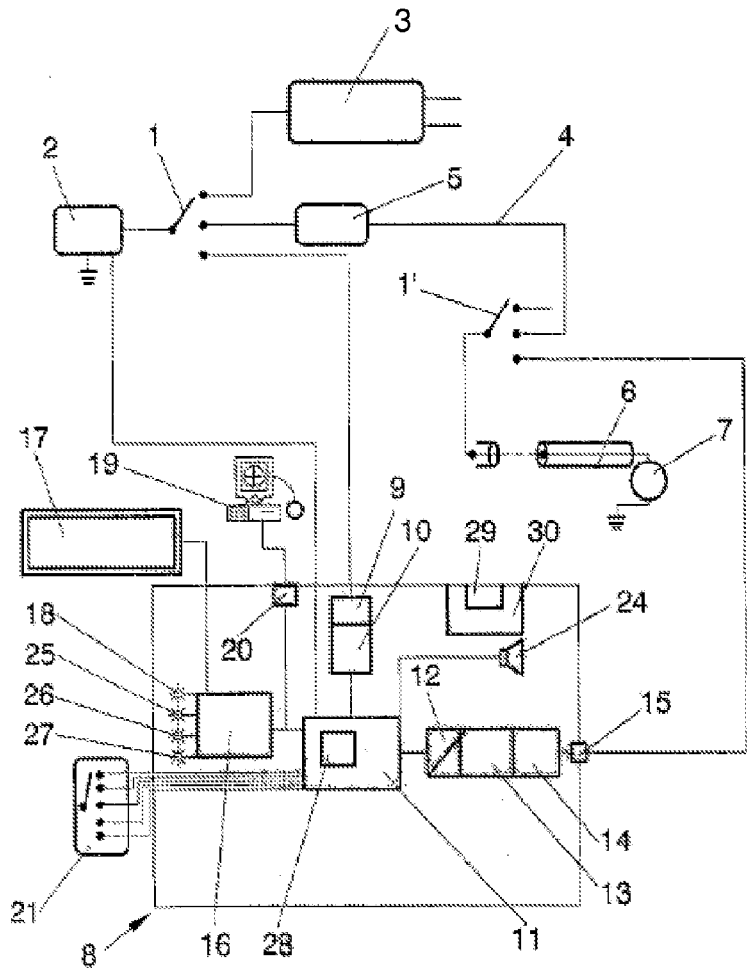

1. Switch
2. Battery
3. Charger
4. Circuit
5. Acoustic device
6. Cable of helmet
7. Coils
8. Stimulation signal generator
9. Voltage regulator
10. Voltage convertor
11. Microcontroller
12. Digital to analog converter
13. Current/voltage converter
14. Conversion stage
15. Specialized connector
16. Second microcontroller
17. Display
18. Battery indicator light
19. External device
20. Connection port
21. Program selector
22. Not used
23. Not used
24. Speakerphone
25. Low battery indicator light
26. Application in process indicator light
27. Regulator connected indicator light
28. Internal program
29. Special connector microcontroller
30. Special connector

BIOPHYSIOLOGICAL REGULATOR FOR THERAPEUTIC TREATMENTS

OBJECT OF THE INVENTION

The invention, as expressed in the present descriptive written paper, refers to a biophysiological regulator for therapeutic treatments.

More specifically, the object of this invention is a regulatory device, attached to a series of coils through which current flows and through a microcontroller generates a low frequency magnetic field, which provides a brain stimulation, being specially designed, thanks to the internal software configuration and the layout of the controls, in order to be applied as therapy in case of fibromyalgia and other such disorders, directly by the patients who suffer them, having means for adjusting both the frequency and the typology of the output wave and the application time for the same.

The controller incorporates, likewise, a second microcontroller responsible for monitoring the level of battery load, to keep count of the sessions (done and available), to show the user name, etc. in a liquid crystal display, besides incorporating a number of programs in its internal memory which provide it with a completely autonomous character.

In addition, the regulator presents a configuration in which different functions are separated from the system so that it can be easily located and replaced at any stage in case of a possible malfunction.

The device also allows to provide information about the data concerning the session without connecting it to an external device, as well as choosing from a series of predefined or mixed programmes.

Moreover, the regulator, to be described later, includes a key switch which allows the computer user to disable the stimulation function regardless of the load and verification of continuity.

Finally, it is to be emphasized that the regulator, which is extolled of having a battery supply, does not necessarily depend on an external device, may, however, be complemented with an external device, so that the use of reduced dimensional components makes it a portable device.

FIELD OF APPLICATION

The field of application of this invention is for the industries involved in the manufacture of instruments and/or therapeutic devices, especially for the treatment of diseases affecting the brain.

BACKGROUND OF THE INVENTION

In therapies, for the cure of brain diseases, low-intensity and low frequency stimulators are used commonly, constituted essentially by a magnetic field generator that connects stimulation coils.

Likewise, and as a reference to the technical condition, the petitioner is aware of the patent P200501477 related to a device type mentioned here, which incorporates a series of coils arranged in an applicator cap where current is generated by a digital microcontroller which is powered by an external source through a voltage regulator, incorporating a program in its memory, responsible for generating different types of waves through the parameters sent by a computer to which it is connected.

To check the proper operation/functioning of the cable and the coils, in an additional certificate to the said patent, a circuit or an intermediate stage is incorporated for the improvement of the same in the implementation process which generates a signal that alerts if it is not in a perfect condition.

The aforementioned stimulator as well as other known devices introduces as fundamental problem, the dependence on a computer unit for the introduction of the stimulation parameters, limiting the portability chances. Likewise, it does not allow to visualize the information for its use or the level of battery charge.

Moreover, one of the other disadvantages of such devices lies in its internal configuration where the different functions are not separated from the system which complicates to a large extent the operations related to location and replacement which could result in the malfunctioning of the device.

Finally, it is noteworthy that these devices suffer, as the main problem to resolve, from a lack of frequency regulation and typology of the output wave appearing from the different pre-recorded selectable programs incorporated in it.

Therefore, the aim of this invention is to provide a better solution and alternative to the problems described, to be mentioned that, on behalf of the applicant, the existence of any other similar device with similar/equivalent technical structural characteristics and configuration is totally unknown to the applicant.

SUMMARY OF THE INVENTION

For this and in a concrete manner, the biophysiological regulator for therapeutic treatments, that the present invention proposes, is based on the conventional structure that has a switch through which a voltage regulator is fed electrically, which in turn, is connected to a converter, coupled to a microcontroller compatibly connectable to a computer, which through a converter converts the digital signal into an analogue to be conducted to a converter that converts it into voltage so as to pass through a conversion stage to current source independent of the charge, connecting it to the anticipated coils under a hat or helmet and which generates the magnetic field applied to the patient, in a distinct manner it incorporates a connection port that allows the introduction, in a second microcontroller, of the stimulation parameters: wave type, frequency, time, current, number of sessions, warning sound or not, number of warning sound and types of programs, which can be simple or mixed.

This second microcontroller is linked to a liquid or similar type crystal display, through which it can display the level of battery charge, counting session of both that were used by the patient as well as the remaining ones, and display the user name. All this adds to its autonomous character.

The regulator also has an acoustic signal speaker, indicator for the end of the application controlled by the software programming; a stage of battery recharging that can be internally integrated, and a series of warning LED lights whose function is to alert the users about the current state of the functionality of the generator. A battery charging LED which lights up when charging, turns off automatically when the battery is fully charged or, alternatively changes its colour in the said circumstances. A connection LED remains on when the generator is on. And an application LED which blinks when the regulator is pursuing a session, and a low battery LED.

Biophysiological regulator, as described, has a compact portability format which is applied through a treatment helmet built in plastic or a suitable textile equipped with a disposable hygienic internal cover, which has coils in series, sequential and orderly distributed under established criteria. These coils consist of a bracket with a rod that passes through the cap and passes through the centre hole of the coil spool, with a closing system "click" that makes the coil fixed on the cap.

There is also a distinct internal program with regulatory capacity both in frequency and the typology of the output wave, the program being recorded within the microcontroller which is powered by the battery of its own device and its operation is governed by the appropriate program according to an application time control, and stopping automatically at the end of the application.

The regulating device of the invention has also, given its portable character, the helmet's configuration and its use, the advantageous feature of this configuration is the direct application of this device by the patient, thus allowing the patient to self-apply the treatment, especially being applicable in the cases of fibromyalgia and other health conditions, and incorporating moreover an inviolability system which consists of a microcontroller within a special connector that is incorporated into the entire device (applicator and cable). The internal software of the device reads the serial number located inside the microcontroller of the connector, ensuring, that it should be an authorized number for future applications so that they can be used by authorized persons.

Furthermore, it is important to note the manner in which the regulator uses the parameters of stimulation in different pre-defined programs, which is done in such a way that each one of them receives a separate set data to identify the type of application, i.e. a program with a different frequency, time and power than the other. In the case of joint programs, a whole set of parameters (different frequencies, time and currents) is sent to a single pre-defined program, and during a session, different frequencies can be applied to variable current and time.

All this is done between an external device and the microcontroller which is incorporated to regulator. The device transmits data frequency, currents and time that will be used by predefined programs or mixed programs, even by the regulator. The microcontroller receives this data and keeps it in its eeprom internal memory. Once the data is stored there, the user has the option to select the type of application s/he may wish to use, if it's a preset program which has a single frequency, time and power, or will it be a joint program where different time, currents and frequencies may exist for the application.

Further it is to be noted that the medium of transmission of the data used by the regulating device of this invention could be wireless through Bluetooth. For this purpose, the regulator contains an internal device which receives the signal through the communication means. This device is a chip built into the printed circuit of the regulator, and its function is to demodulate the incoming signal and transfer the data to the microcontroller through the communication channels of the controller circuit board.

Finally, the biophysiological regulator for therapeutic treatments presents different stages of functionality, which can be controlled by/through switchboards at various positions, where each one of them defines a state. These states are: "off", when the circuit is completely disconnected from the supply battery and the stimulation cap; "load", when the circuit is only connected to a battery charger; "continuity", when the battery, the stimulation cap and a coil are connected and which will beep indicating the good functioning of the circuit of the cable and the coils; "application", when the battery, the cap, the printed circuit components, the circuit cable and the applicator cap are connected. At the end of a session, the speaker beeps as many numbers of times as it has been programmed by the programming software of the regulator.

The new biophysiological regulator for therapeutic treatments introduces, thus, innovative structural and constituent features hitherto unknown for this purpose, reasons linked to its practical utility, which provides with enough bases to get the prerogative of exclusive right.

DESCRIPTION OF THE DRAWING

To complement the description being made here and in order to help better understanding of the innovative features, a set of drawing is attached herewith this descriptive written paper, as an integral part of the same, in which the following is represented in an illustrative manner and not in a limiting manner as follows:

FIG. 1—Shows a diagrammatic representation of the subject matter, i.e. biophysiological regulator for therapeutic treatments, in which the main parts and its constituent elements as well as the configuration and layout of the same can be seen.

PREFERENTIAL EXECUTION OF THE INVENTION

In view of the above FIG. 1, and according to the numbering adopted therein, one can observe how the biophysiological regulator for therapeutic treatments contains a double switch (1) (1'), a battery (2), a charger (3), that feeds a circuit (4) equipped with an acoustic device (5) connected to cable (6) of the helmet equipped with coils (7), a stimulation signal generator (8) which in turn incorporates a voltage regulator (9), a voltage converter (10) linked to a microcontroller (11) with a digital to analogue converter (12), a current/voltage converter (13) a conversion stage (14), inviolability specialized connector (15), besides incorporating a second microcontroller (16), a liquid crystal display (17) a pre-recorded programs selector (21) and a connection port (20) for introducing the parameters through an external device (19), a speakerphone (24) and a series of bright LED battery indicators (18), regulator connected (27),and application in process (26), besides incorporating an internal program (28) that regulates both the frequency and typology of the output wave and time of each pre-recorded program.

When the voltage of the battery (2) falls below a preset value, a visual alarm will be produced by blinking the low battery LED (25) so that the user notices the situation and sets it for recharge.

The stage of charging or charger (3) of the battery (2) may be integrated internally in the device, or interchangeably could be an external element without affecting the essence of the invention, providing in any case, the necessary cable for connecting it to the mains/power supply.

Moreover, the signal generator (8) has the capacity to generate four types of waves: square, sine curve, saw tooth, and triangular, being scalable, unlimitedly, through a simple process of a new transmission of data from the external device, indicating the type of wave to be used.

The selected and emitted current, through the current source independent of the load, could be a coil, as is the case of experimentation at neuronal level in vitro, or various coils connected in series, as is the case of cap coils used for magnetic application at human level. The current range may exceed the 2000 vA.

Parameters such as stimulation frequency, current that circulates through the coils (7), stimulation time and typology of wave, are introduced through the said external device (19), for which the generator (8) has the corresponding connection port (20), providing ability to detect whether or not it is connected to an external device, so that if it is the former case, it will wait for the incorporation of the new stimulation parameters from the device (19) and will store it in the EEPROM memory of the microcontroller (11). In latter case, the stimulation parameters will be read from the mentioned EEPROM memory so that it is not necessary to dependence on an external device all the time.

Moreover, in order to provide an audible signal indicating the patient or the user about the completion of the stimulation time, the device includes a speaker (24) controlled by a programmed software through which a beep sound will be emit, repeating as many times as it has been programmed to indicate the end of the session.

Finally, the circuit (4) is linked to a key switch, not shown in the drawing, which allows the computer user to disable the stimulation function, while the other functions of loading and verification of continuity are enabled.

The device incorporates, as mentioned earlier, an inviolability system that consists of a microcontroller (29) inside a special connector (30) which is incorporated in the regulating device set, i.e. cap applicator and cable (6), in which the internal software of the device reads the serial number located inside the microcontroller of the connector, ensuring that it should be an authorized number for all future applications so that the device can be used only by authorized persons.

The regulator offers a compact format portable application format through a treatment helmet built in an appropriate fabric, provided with a disposable internal sanitary sheath, having coils (7) in series, sequential and orderly distributed under established criteria, which consist of a bracket with a rod that passes through the cap and passes through the centre hole of the coil spool, with a locking system "click" that makes the coil fixed to the cap.

The nature of the present invention as well as how to implement it is sufficiently described. Hence, it is not considered necessary to provide further explanation here so that any expert in the concerned field can understand its field of application and the benefits derived from it result. It is also to be stated that, in its essence, it can be put into practice in other embodiments that may differ in detail from the one indicated as example, and which are also within the reach of the protection provided its fundamental principle is not altered, changed or modified.

The invention claimed is:

1. BIOPHYSIOLOGICAL REGULATOR FOR THERAPEUTIC TREATMENTS, those used in therapies based on magnetic waves, applicable to any cerebral disease and can be used directly by the patient so that the patient can self-apply the treatment, in which a series of coils for brain stimulation are involved, through which a current is circulated that generates a magnetic field of low frequency; current generated by a digital microcontroller which is fed by a power supply, with a pre-recorded programs selector, and a connection port for introducing the parameters through an external device, characterized by the fact that the biophysiological regulator comprises of a second microcontroller, a liquid crystal display, containing a speaker and a series of bright LED battery indicators, connected regulator, application in process, and low battery, and with an internal program that regulates both the frequency and typology of the output wave and the application time for each pre-recorded program; further comprising a compact portable application format through a treatment helmet built in an appropriate fabric, provided with an internal disposable sanitary sheath, having coils in series, sequential and orderly distributed under established criteria, which consist of a bracket with a rod that passes through a cap and passes through the centre hole of a coil spool, with a locking system that makes a coil fixed to the cap.

2. BIOPHYSIOLOGICAL REGULATOR FOR THERAPEUTIC TREATMENTS, those used in therapies based on magnetic waves, applicable to any cerebral disease and can be used directly by the patient so that the patient can self-apply the treatment, in which a series of coils for brain stimulation are involved, through which a current is circulated that generates a magnetic field of low frequency; current generated by a digital microcontroller which is fed by a power supply, with a pre-recorded programs selector, and a connection port for introducing the parameters through an external device, characterized by the fact that the biophysiological regulator comprises of a second microcontroller, a liquid crystal display, containing a speaker and a series of bright LED battery indicators, connected regulator, application in process, and low battery, and with an internal program that regulates both the frequency and typology of the output wave and the application time for each pre-recorded program; further comprising an inviolability system consisting of a microcontroller inside a special connector which is incorporated in a set, applicator and cable, in which an internal software of the external device reads a serial number located inside the microcontroller of the connector; and a compact portable application format through a treatment helmet built in an appropriate fabric, provided with an internal disposable sanitary sheath, having coils in series, sequential and orderly distributed under established criteria, which consist of a bracket with a rod that passes through a cap and passes through the centre hole of a coil spool, with a locking system that makes a coil fixed to the cap.

* * * * *